Figure 1:
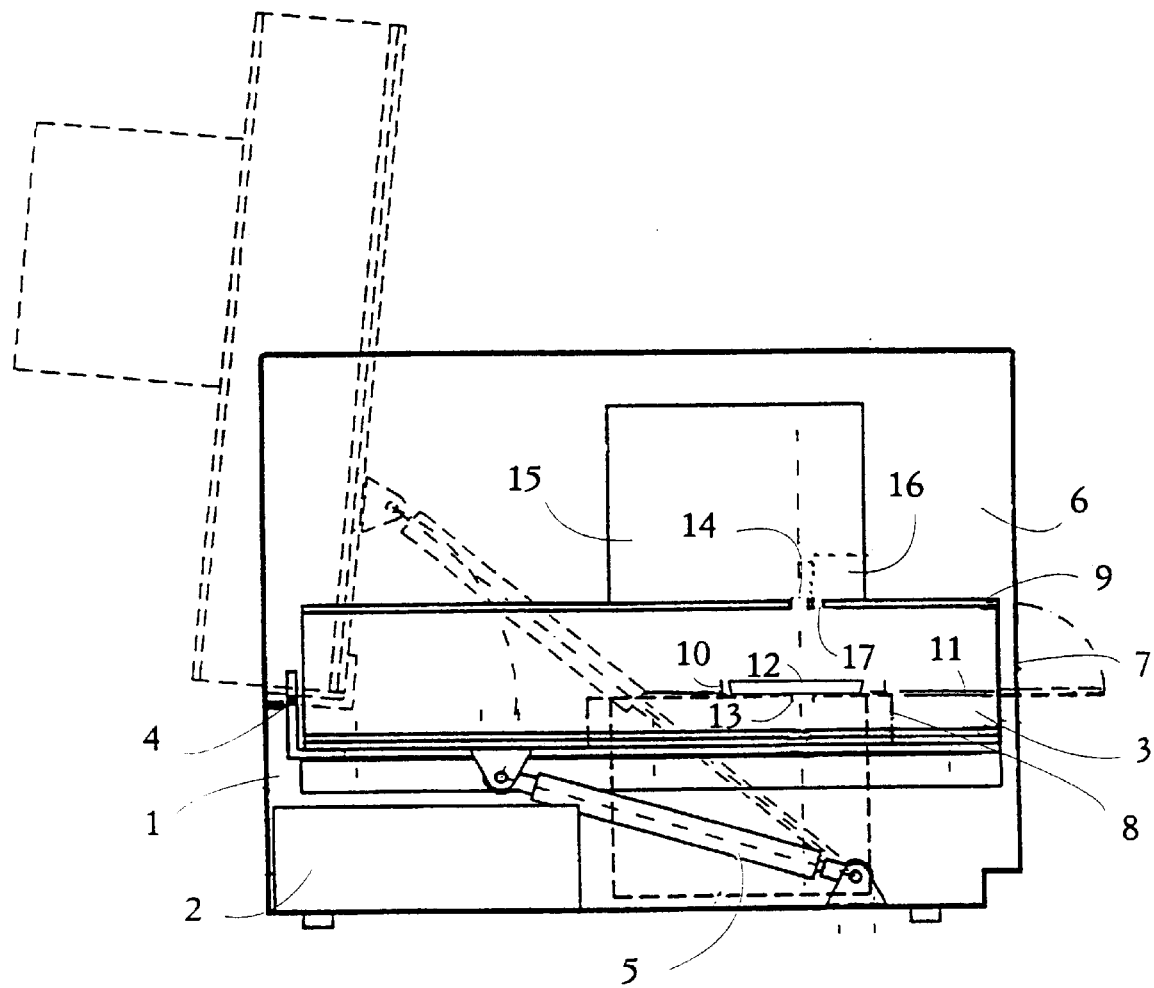

United States Patent
Tuunanen et al.

[11] Patent Number: 6,144,455
[45] Date of Patent: Nov. 7, 2000

[54] FLUOROMETER

[75] Inventors: Jukka Tuunanen; Timo Kärmeniemi, both of Helsinki, Finland

[73] Assignee: Labsystems Oy, Helsinki, Finland

[21] Appl. No.: 09/043,596

[22] PCT Filed: Sep. 20, 1996

[86] PCT No.: PCT/FI96/00498

§ 371 Date: Mar. 20, 1998

§ 102(e) Date: Mar. 20, 1998

[87] PCT Pub. No.: WO97/11354

PCT Pub. Date: Mar. 27, 1997

[30] Foreign Application Priority Data

Sep. 22, 1995 [FI] Finland .................................... 954511

[51] Int. Cl.[7] ............................ G01J 3/46; G01N 33/566
[52] U.S. Cl. .......................... 356/402; 356/344; 436/501
[58] Field of Search .................................. 356/417, 246, 356/317, 73, 344, 440, 445, 402; 436/501, 172, 48

[56] References Cited

U.S. PATENT DOCUMENTS

| | | |
|---|---|---|
| 3,421,821 | 1/1969 | Alessi . |
| 4,053,235 | 10/1977 | Hampton et al. . |
| 4,117,338 | 9/1978 | Adrion et al. . |
| 4,150,295 | 4/1979 | Wieder . |
| 4,426,154 | 1/1984 | Steen . |
| 4,501,970 | 2/1985 | Nelson . |
| 4,945,245 | 7/1990 | Levin . |
| 4,945,250 | 7/1990 | Bowen et al. . |
| 5,091,652 | 2/1992 | Mathies et al. . |
| 5,108,179 | 4/1992 | Myers . |
| 5,147,609 | 9/1992 | Grenner . |
| 5,166,813 | 11/1992 | Metz . |
| 5,360,523 | 11/1994 | Middendorf et al. . |
| 5,482,861 | 1/1996 | Clark et al. . |
| 5,515,169 | 5/1996 | Cargill et al. . |
| 5,639,668 | 6/1997 | Neel et al. . |
| 5,891,738 | 4/1999 | Soini et al. . |

FOREIGN PATENT DOCUMENTS

| | | | |
|---|---|---|---|
| 0 106 662 | 4/1984 | European Pat. Off. | ........ G01N 21/03 |
| 0 108 524 | 5/1984 | European Pat. Off. | ........ G01N 21/64 |
| 0 411 557 A3 | 2/1991 | European Pat. Off. | ........ G01N 21/64 |
| 0 421 156 A3 | 4/1991 | European Pat. Off. | ........ G01N 21/64 |
| 0 521 636 A1 | 1/1993 | European Pat. Off. | ........ G01N 21/64 |
| 0 640 828 A1 | 3/1995 | European Pat. Off. | ........ G01N 21/64 |
| 145176 | 10/1981 | Norway . | |
| 2 088 580 | 6/1982 | United Kingdom . | |
| 2 196 734 | 5/1988 | United Kingdom . | |
| 2 264 558 | 9/1993 | United Kingdom | ........... G01N 21/64 |
| WO 82/00356 | 2/1982 | WIPO . | |
| WO 82/00361 | 2/1982 | WIPO . | |
| WO 83/00931 | 3/1983 | WIPO . | |
| WO 92/22801 | 12/1992 | WIPO . | |

OTHER PUBLICATIONS

International Search Report, Application No. PCT/FI 96/00498, (Jan. 1, 1997).

International Search Report for PCT/FI96/00497 (Jan. 1, 1997).

Primary Examiner—Frank G. Font
Assistant Examiner—Roy M. Punnoose
Attorney, Agent, or Firm—Fish & Richardson P.C.

[57] ABSTRACT

A fluorometer has a partly transparent mirror through which excitation light is directed to the sample and via which emitted light from the sample is reflected. Thus a high sensitivity and, furthermore, as homogenous a measurement sensitivity distribution as possible within a vessel are achieved. Measuring can be carried out from either above or below. The device is applicable for use especially when the fluorometer has simultaneously a plurality of samples.

25 Claims, 6 Drawing Sheets

FLUOROMETER

FIELD OF TECHNOLOGY

The invention relates to instrument technology and concerns fluorometers used in laboratories, which fluorometers can be used, for example, in assays of clinical chemistry and food technology. The invention is particularly suited for use in fluorometers having simultaneously a plurality of samples.

BACKGROUND

In a fluorometric assay there is directed to the sample a short-wave excitation light, which makes the substance being assayed to emit longer-wave light. The quantity of the emitted light is measured, and thereby the quantity of the substance being assayed is detected. In general, a fluorometer has one measuring channel and the assays are performed on plates having multiple wells. In this case the plate is moved relative to the measuring channel in such a way that each well in turn arrives at the measuring position.

The background fluorescence caused by excitation light incident outside the sample being assayed constitutes one problem with fluorometers. This can be reduced by using non-transparent shields. In practice, however, it is difficult to obtain sufficient light-tightness in this manner.

Fluorometric measuring through a vessel is not especially recommendable, since in such a case there passes through the vessel also a large amount of excitation light, which complicates the measuring of emitted light. Background fluorescence possibly caused by the material of the vessel constitutes a further problem. In most fluorometers currently used for routine assays, excitation light is directed to the vessel from above, and also emitted light is collected from above. In certain assays it is, nevertheless, best to carry out the measuring through the bottom of the sample-holding vessel.

From publication EP-A-108524 there is known a fluorometer measuring from above. Therein the excitation light is delimited by means of an aperture, a diverging beam of light is converged by means of a lens, and the converging beam of light is directed via a filter and a mirror as a spot to the sample-holding vessel. The emitted light, respectively, is directed from the vessel via another mirror, filter, converging lens and delimiting aperture to a detector.

From publication EP-A-640828 there is known a fluorometer measuring from above, wherein excitation light is directed simultaneously to a plurality of samples through a dichroic mirror, and emitted light from the sample vessels is reflected via the same mirror to a camera.

DESCRIPTION OF THE INVENTION

General Description

A fluorometer according to claim 1 has now been invented. Preferred embodiments of the invention are stated in the other claims.

According to the first characteristic of the invention, the fluorometer has a partly transparent mirror. In this case the axis of the excitation channel and the axis of the emission channel coincide between the mirror and the sample, and the solid angle of the entire aperture of the sample-holding vessel can be exploited. Thus there is achieved a high sensitivity, as well as inside the vessel a maximally homogenous measuring sensitivity distribution. The measuring can be carried out from either above or below.

No particularly large lenses or filters are required for implementing the system according to the invention.

The partly reflective mirror may have a dichroic dielectric film. Such films, however, in general perform only within a very narrow wavelength range (e.g. 400 . . . 600 nm), which is not sufficient in nearly all fluorometric assays. The mirror should perform within a range of, for example, 260 . . . 800 nm. A wide-band dichroic mirror can be made by vaporizing onto a glass surface a thin film partly transparent to light. However, such a film causes a great deal of losses. Preferably, a mirror is used which is made up of completely reflective and completely transparent areas. Such a mirror is easy to manufacture by vaporizing, for example, aluminum onto the surface of suitable glass. A very wide wavelength range can be achieved by using such a mirror, and the reflection capacity or transparency is not significantly dependent on the wavelength. Also, polarization does not occur in this mirror in the manner occurring in dichroic films. Furthermore, the shape of the reflective areas can be exploited in the optics, for example, to eliminate the effect of reflection or diffraction.

Excitation light which has been reflected from the mirror or which has passed through it can be used as a reference light to eliminate errors due to variations in the source of light. A possible excitation light filter is in this case preferably positioned at a point before the mirror.

According to one independent characteristic of the invention, the fluorometer has in the excitation channel a lens arrangement by means of which a unidirectional beam of excitation rays is formed. The apparatus preferably also has a converging lens arrangement by means of which, from the unidirectional light beam, a delimited spot of excitation light is formed on the object being assayed. Thus fluorescence occurring outside the desired measuring region is decreased.

According to a second independent characteristic of the invention, the fluorometer has in the emission channel a lens arrangement by means of which a unidirectional beam of light is formed from the emitted light. The apparatus preferably also has means for directing emitted light into the emission channel only from a delimited region. Thus detection of emission occurring outside the desired measuring region is reduced. Preferably the apparatus has both emission delimiting means and excitation delimiting means. In this case there may be closest to the object being assayed a lens system which functions as a part common to both.

The wavelength of the unidirectional beam of light can be delimited effectively to the desired wavelength range by means of filters. This concerns in particular inference filters.

According to a third embodiment of the invention, the fluorometer has an excitation light delimiting arrangement which comprises an excitation light delimiter and means for forming an image of the light source on the delimiter. By means of the delimiting arrangement, a veil caused by reflective and refractive surfaces of the source of light can be eliminated, and thus excitation light can be directed as precisely as possible only to the desired region. Lens or mirror optics can be used in the arrangement. From the delimiter the light can be directed further in a controlled manner to the sample. From the aperture of the delimiter there is preferably formed an image in the desired measuring region, and thus fluorescence occurring outside the desired region is eliminated. Preferably the delimiter is replaceable, in which case an excitation region of the desired shape and size is obtained in the sample at each given time.

According to a fourth independent characteristic of the invention, the fluorometer has an emitted light delimiter, an arrangement for forming in the aperture an image of the delimited region of the sample, and a filter at a point after the aperture. Thus the quantity of light arriving from the outside at the desired region is reduced and the filtering can be easily arranged in the desired manner. The delimiter is preferably replaceable, in which case the size or shape of the delimiting aperture can be varied, and thus measuring light can be collected from a region of the desired type at each given time. Preferably the image-forming means comprise a lens system for converging the light emitted from the sample, a mirror to which the converged beam of light is directed, and another converging lens for forming in the delimiter aperture an image of the light reflected from the mirror.

According to a fifth independent characteristic of the invention, the fluorometer has an arrangement for eliminating errors caused by variations in the distance to the object being assayed. The arrangement comprises a lens system for collimating the emitted light and a delimiter by means of which scattered rays are delimited out from the beam of light.

According to a sixth independent characteristic of the invention, the apparatus has, capable of being positioned either above or below the apparatus, an optics module having both a source of light and a detector. Thus the apparatus can be used for performing the measuring from either above or below, according to need. However, fiber optics is not required in the apparatus for directing light to the detector, since the required optical means are part of the movable module and can thus be mounted fixedly relative to the detector. The avoidance of fiber optics is a particular advantage, since fiber optics usable within the UV range is especially expensive. Fiber optics also causes background fluorence, which can thus according to the invention be avoided.

According to a seventh independent characteristic of the invention, the source of light is replaceable in such a way that the source of light may be a light bulb or a fiber bundle head by means of which excitation light is introduced to the excitation optics from the exterior.

The light source used is preferably an incandescent bulb, provided that sufficiently short-wave radiation suitable for the purpose is obtained by means of it. An incandescent bulb does not require special arrangements and, furthermore, a delimited image thereof is easy to form by using the luminosity of the entire bulb.

The apparatus is preferably such that samples held in different vessels can be assayed therein. Sample vessels usually form an entity of a plurality of vessels, for example a microtiter plate. Preferably the apparatus has a movable measuring carrier for the samples, by means of which carrier each sample in turn is taken to the measuring position. By suitable movement of the carrier the samples may, when so desired, also be agitated. So-called scanning measuring can also be carried out by moving the samples.

DRAWINGS

Figure 2A:
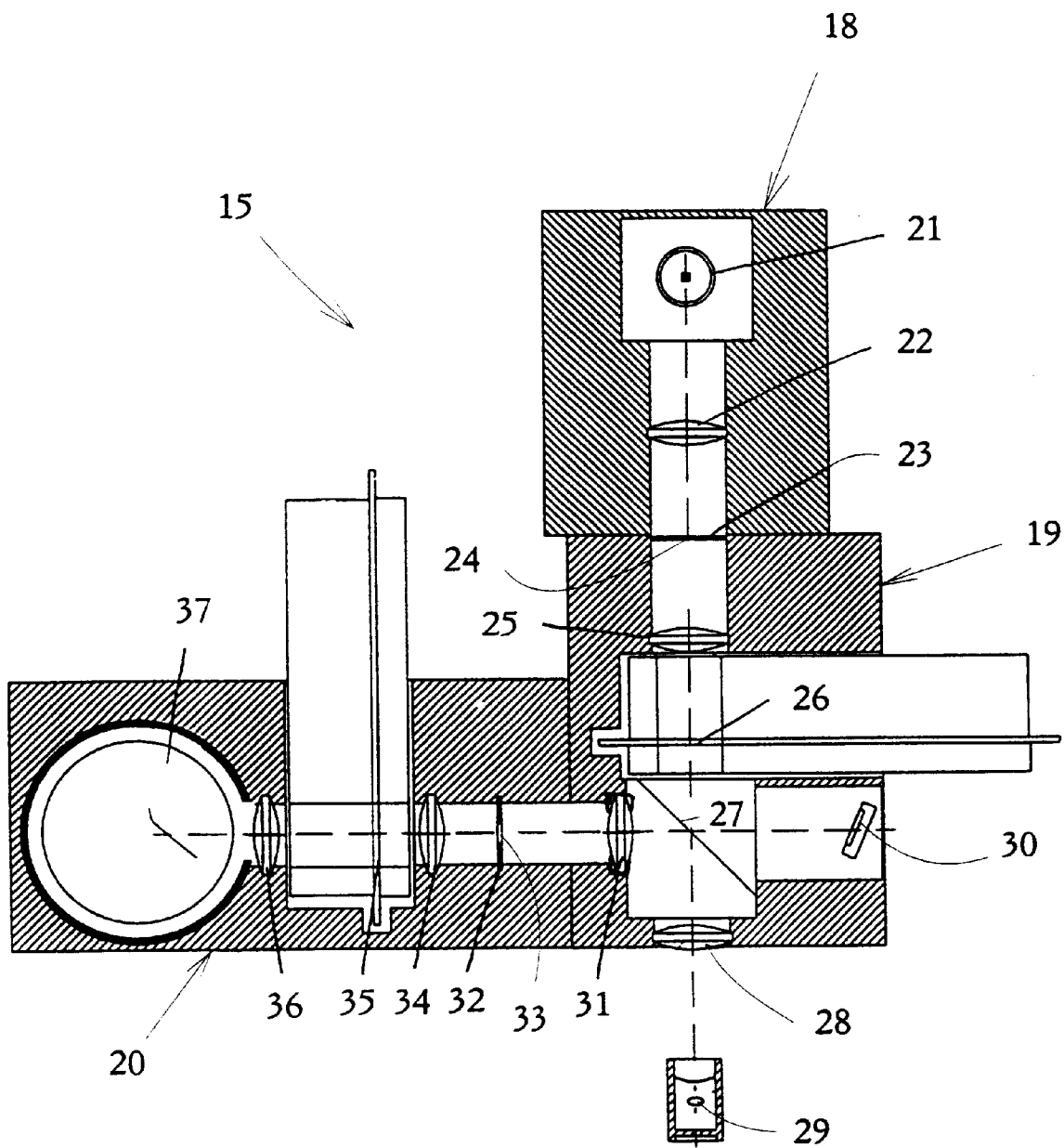
Figure 2B:
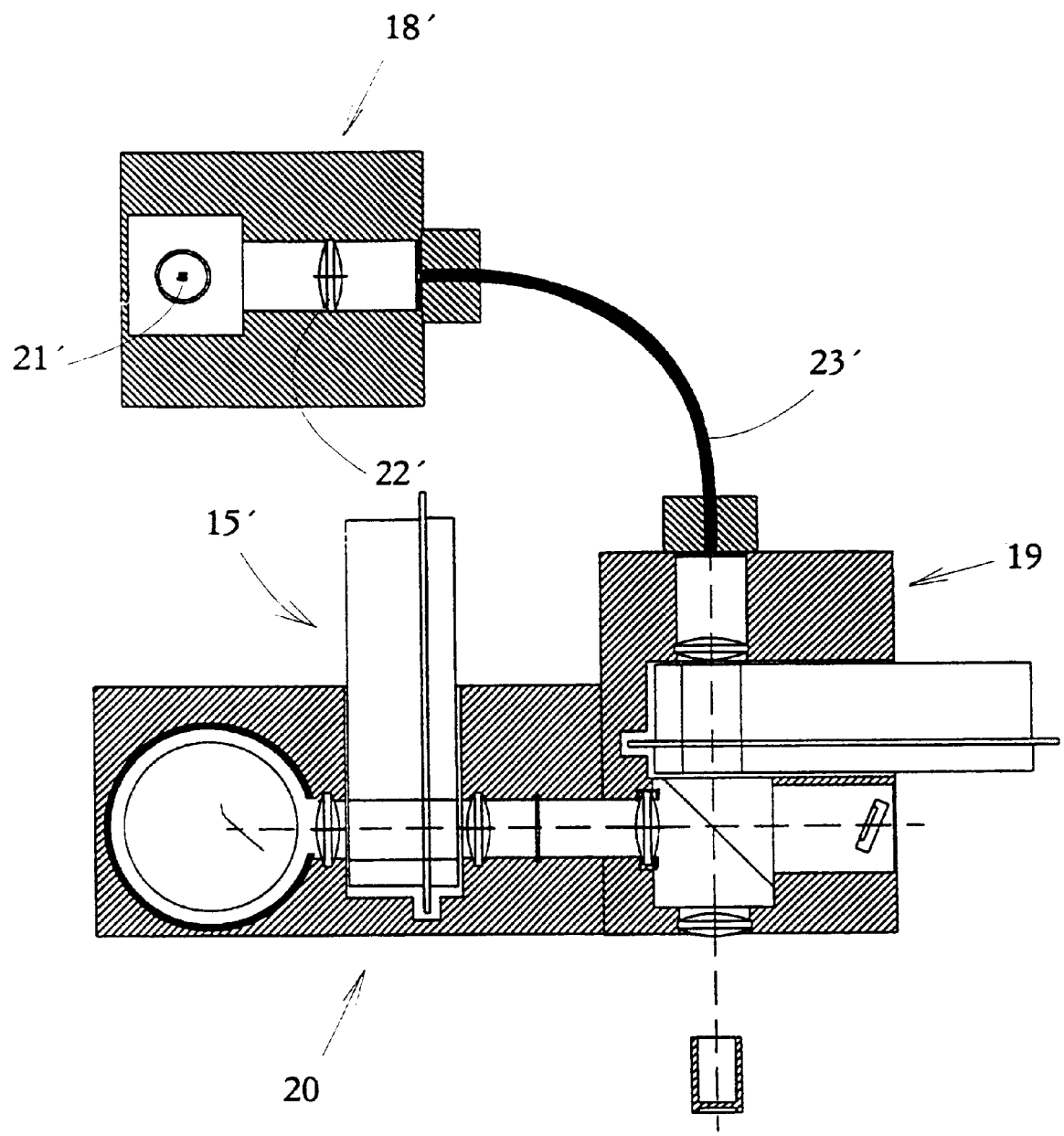
Figure 3:
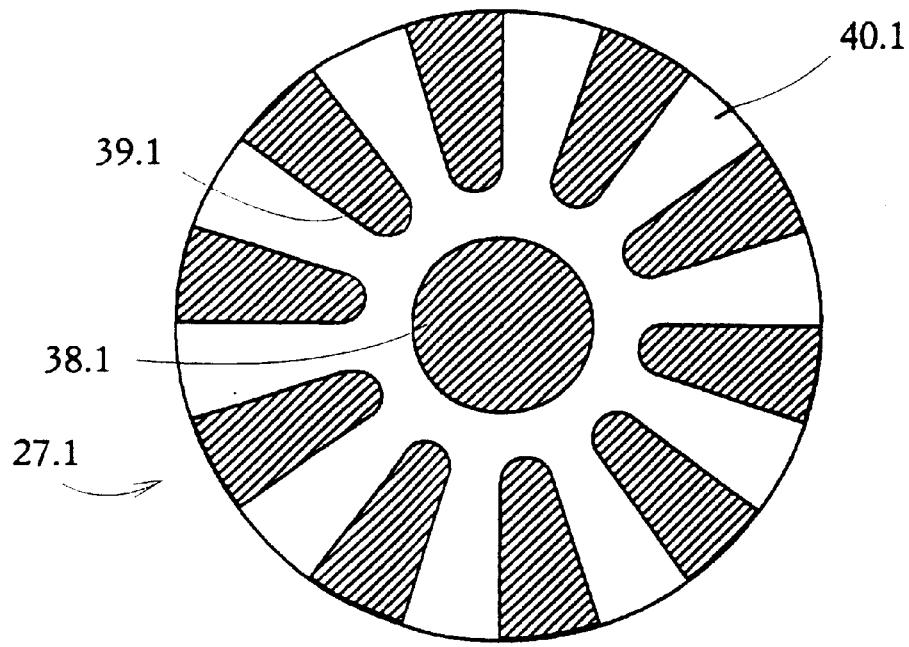
Figure 4:
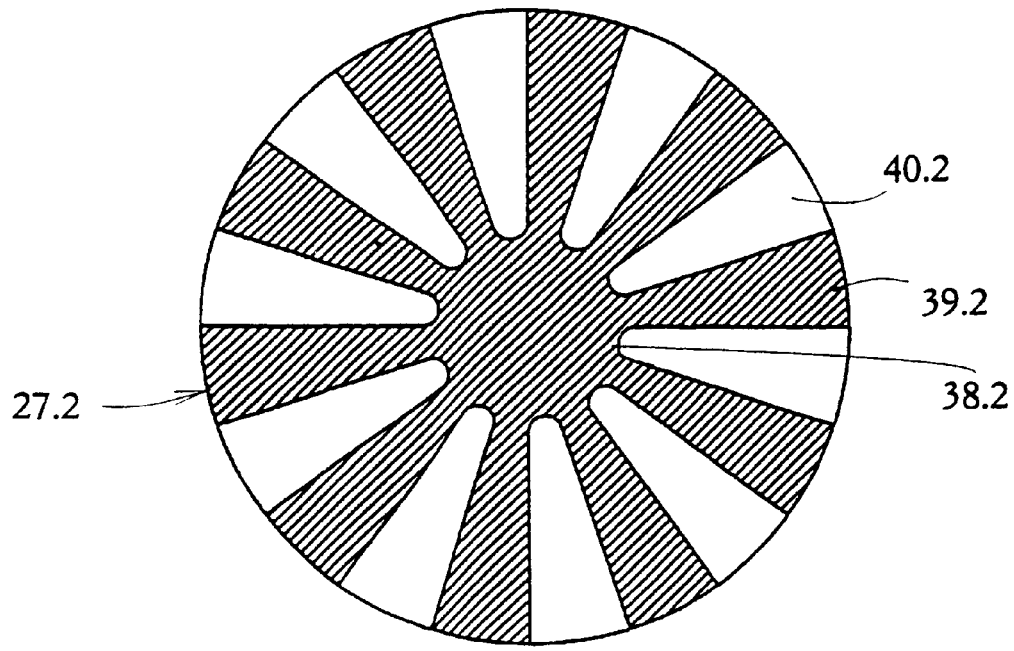
Figure 5:
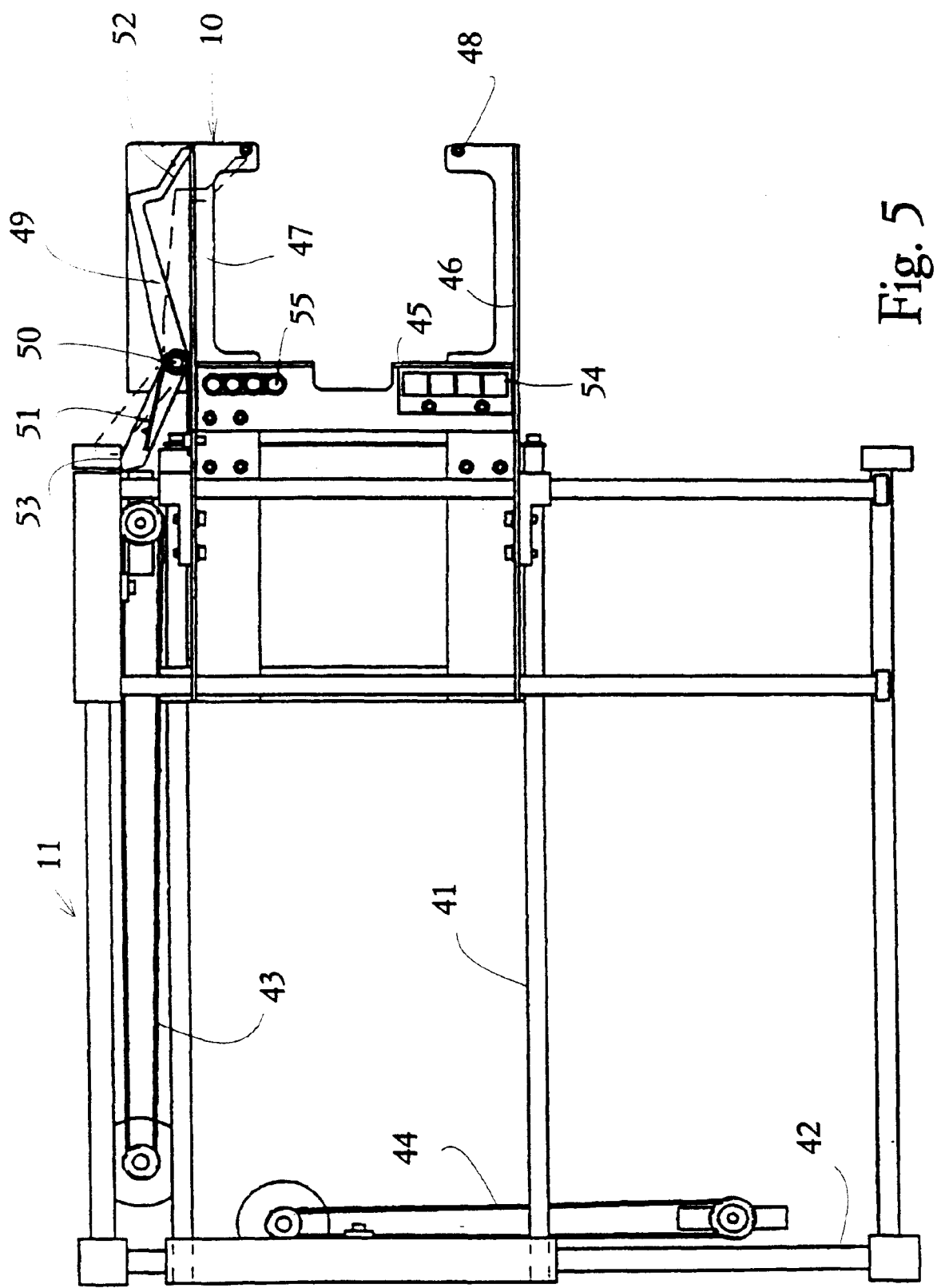
Figure 6:
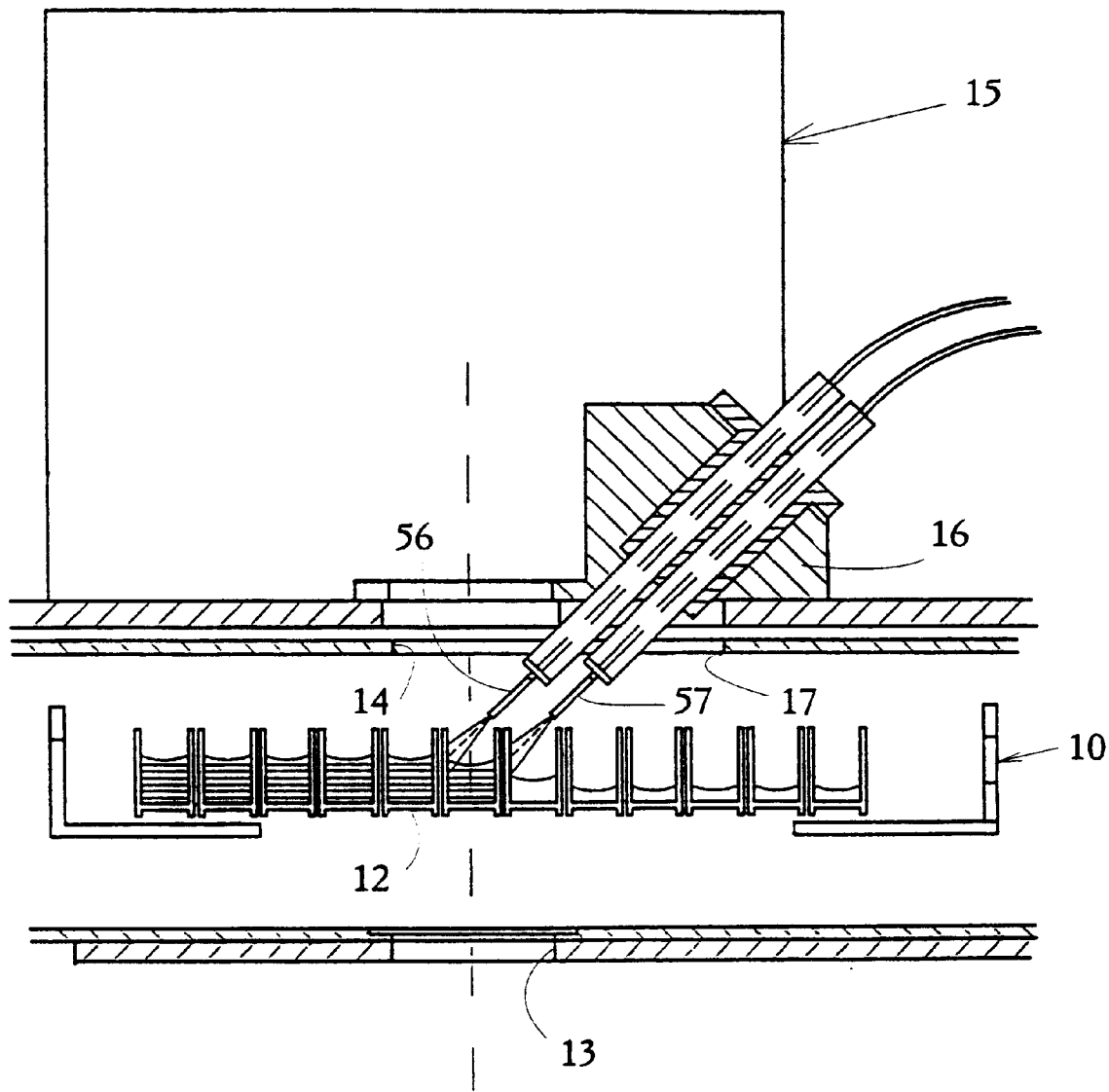

The accompanying drawings constitute part of the description of the invention. Therein FIG. 1 depicts a side elevation of one fluorometer according to the invention, FIG. 2a depicts the optics arrangement of the fluorometer of FIG. 1, FIG. 2b depicts an alternative optics arrangement, FIG. 3 depicts one mirror usable in the optics arrangement, FIG. 4 depicts another mirror usable in the optics arrangement, FIG. 5 depicts a plan view of the sample plate transfer arrangement of the fluorometer of FIG. 1, and FIG. 6 depicts a detail of the fluorometer of the figure, with a plate in the dispensing and measuring position.

SPECIFIC DESCRIPTION

The fluorometer of FIG. 1 has a lower housing 1, which houses, among other things, a control unit 2 and connections to the power source and to functions external to the apparatus. On top of the lower housing there is a light-tight measuring unit 3. Its back edge is hinged 4 to the back edge of the lower housing so that the measuring unit can be pivoted upwards, whereupon there will be easy access to the parts below it. The pivoted measuring unit is held in the upper position (shown by dotted lines in FIG. 1) by a pneumatic spring 5. Above the lower housing and the measuring unit there is a detachable upper housing 6. In the front wall of the measuring unit and the upper housing there is an aperture 7 equipped with a light-tight hatch, through which aperture the samples are transferred into the measuring unit and out of it.

The measuring unit 3 has a lower deck 8 and an upper deck 9. In the space between these a measuring carrier 10 is moved by transfer means 11. The plate 12 with the samples to be assayed is placed in the measuring carrier. The measuring carrier can be moved out through the aperture 7.

In the lower deck 8 of the measuring unit 3 there is a lower measurement aperture 13 and in the upper deck 9 an upper measurement aperture 14. The measuring unit has an optics module 15, which may be placed either above or below the measuring unit. The upper deck additionally has a liquid dispensing unit 16 and a dispensing aperture 17, through which liquids can be dispensed into the wells of the plate 12.

The principal parts of the optics module 15 are a light source unit 18, a mirror unit 19, and a detector unit 20. The optics module is used for directing both excitation light to the sample and emitted light from the sample, from either above or below.

The light source unit 18 has an incandescent bulb 21; an image of the filament of the bulb is condensed by means of a lens system 22 to the aperture 24 of an excitation delimiter 23 in the mirror unit 19. It is preferable to keep the bulb switched on only during measuring, in order to increase its useful life.

The excitation light coming from the aperture 24 is collimated using a lens system 25, and the collimated light is directed through a filter 26 to a partly transparent mirror 27. By means of the filter the wavelength of the excitation light is delimited to the desired range.

The light which has passed through the mirror 27 is converged via a focussing lens system 28 to the sample. Thus a spot of light 29 is obtained in a delimited spatial region of the sample.

That portion of the excitation light which is reflected from the mirror 27 is directed to a reference detector 30. By means of it any errors caused in the measurement results by variation in the intensity of the excitation light are compensated for. A representative sample of the excitation light is obtained from the mirror. When one-half of the light is used for excitation, the other half can be exploited for defining the excitation amplitude. A unidirectional beam of light may be directed to a detector having a large surface area or, by means of a converging lens, to a smaller detector.

The light emitted from the spot 29 in the sample travels via the focussing lens system 28 to the lower surface of the mirror 27. From the portion reflected from the mirror, an image of the spot is formed, in the aperture 33 of the emission delimiter 32, by means of a converging lens system 31. From the aperture the emitted light is collimated by means of a lens system 34 to a filter 35, from which it is directed via a condenser lens system 36 to a detector 37. By means of the filter, the desired wavelength range is delimited from the emitted light. The filter here is an interference filter. The detector is a photo-multiplier tube.

When the mirror 27 is positioned close to the imaging lens system 28 common to the excitation channel and the emission channel, the image in the mirror is formed at a point far from the object being assayed. When the mirror is at a distance less than the focal distance, no image at all is formed.

The apparatus has a plurality of different excitation filters 26 and emission filters 35. The filters are mounted in a disc, and the desired filter is installed by rotating the disc. The filter discs are also replaceable.

The excitation delimiter 23 is replaceable, and thus an optimal excitation aperture 24 of the desired size and shape can always be placed in the module. The excitation light can thus be focussed, with a good efficiency ratio, precisely on the sample assayed at a given time, or on a preferred or sufficient region thereof. By means of the delimiter it is possible in particular to eliminate disturbances caused by the fluorescence of adjacent samples.

The shape of the delimiting aperture 24 may also vary according to the embodiment. For example, in certain embodiments the fluorescence of an electrophoretically formed line of the sample is to be measured. In such a case, a suitable linear aperture is used.

The user may also, when necessary, visually check the size and shape of the spot of light formed.

The emission delimiter 32 is also replaceable, and thus the light arriving at the detector can be delimited by means of an aperture 33. The light can always be measured from a precisely defined region. This can be used for minimizing background radiation arriving at the detector; such radiation may come in particular from the adjacent wells. The shape of the aperture can also be varied according to the samples to be assayed or their partial regions.

When desired, it is possible to use both an excitation delimiting aperture 24 and an emission delimiting aperture 33 for defining the size and the shape of the measurement region. Often the replacement of only one of the delimiters will suffice, since the disturbing adjacent sample is in any case located outside the area of the wider delimiting aperture. Preferably the excitation light region is made smaller than the emission measurement region.

The emitted light treatment optics described can also be used for eliminating errors caused by variations in the distance to the object being assayed. Such errors may be caused, for example, by curvature of the plate, inclination of the path, and variations in the volume of the samples. Emission sensitivity can be made constant by making the solid angle of the measurement constant. This is achieved by means of an aperture delimiting parallel rays of light, positioned at a point after the mirror 27. In the embodiment of the figure, the retainer of the lens 31 serves as the delimiter. By suitable dimensioning, the depth effect can be almost entirely eliminated.

The light source unit 18 is also replaceable. In its place there can be installed against the delimiting aperture 24 the end of an optical fiber bundle by means of which excitation light is directed from an external source of light. In this case the image is formed of the end of the fiber bundle. This arrangement is used, for example, when a Xe bulb is needed, which requires special safety devices. The specific fluorescence of the fiber used for directing light does not cause problems here, since after the fiber the light passes through an excitation filter 26. FIG. 2b shows such an optics module 15', which has a separate light source unit 18', from which light is directed from bulb 21' by means of a lens 22' and a fiber bundle 23'.

A usable partly transparent mirror 27 can be manufactured by forming reflective spots (diameter, for example, approx. 1 mm) on a glass sheet, these spots covering one-half of the optically transparent surface. The reflective material is preferably aluminum, which has a very wide reflection wavelength range (approx. 200 . . . 1500 nm). The glass sheet is preferably as thin as possible, which minimizes the amount of scattered light due to internal reflections in the glass.

Preferably, however, suitably shaped reflective areas are used. The reflective areas of the partly transparent mirror 27.1 in FIG. 3, the reflective areas are made up of a round center 38.1 and of separate radial sectors 39.1 around it, the transparent area 40.1 being respectively cartwheel-shaped. In the mirror according to FIG. 4, for its part, there is a continuous reflective area made up of a cartwheel-shaped center 38.2 and radial sectors 39.2 linked to it and of a transparent area formed by separate radial sectors 40.2. The central area minimizes the internal reflections of the optics. Owing to the edges of the radial reflective areas, diffraction of light can be caused to take place in the direction of a tangent transverse to the radius.

According to one embodiment, the mirror 27.1 or 27.2 is an oval the 45° projection of which is a circle.

In the transfer means 11 according to FIG. 5, the carrier 10 is mounted so as to slide along longitudinal slide bars 41, which in turn are mounted slidably on transverse slide bars 42. The slide bars can be moved by using motors and belts 43 and 44, and thus the carrier can be brought into the desired position within the measuring unit or out of the aperture in the front wall.

The carrier 10 is rectangular, and it has a back wall 45 and side walls 46. In the lower part of the side walls there are supports 47 so that an open space is left in the center. At the ends of the supports there are inward projections. At the front edge the projections have detachable vertical pins 48. The carrier 10 is dimensioned so that the plate for assaying can be placed to bear on the supports 47 so that the bottoms of the wells are left in the area of the opening. If the plate used is smaller than the opening, a suitable adapter tray is first placed to bear on the supports.

One side edge of the carrier 10 has a plate retainer 49. It is a lever having the basic shape of an obtuse V and being pivoted by its apex to a vertical pin 50 in the carrier. To it there is linked a spring 51, one end of which is against the frame of the carrier and the other end against the retainer so that it tends to turn the outer branch of the retainer towards the center of the carrier (in FIG. 5 clockwise). At the end of the outer branch of the retainer there is a projection 52 towards the carrier. When the retainer is in its released state it presses the plate in the carrier against the back wall and that side wall which is opposite the retainer. Thus the plates always settle in the carrier automatically in the same place against the corner. When the carrier is driven out of the measurement apparatus, the inner branch of the retainer impinges against a stop wall 53 in the transfer apparatus, the stop wall forcing the retainer to turn open. Thus a plate can be placed in the carrier or be removed from it. When the pins 48 are detached, a plate can be transferred to the carrier also along a horizontal path.

The back edge of the carrier 10 has four different fluorescent reference surfaces 54, by means of which the sensitivity of the detector can be checked when so desired.

FIG. 6 depicts the dispensing of liquid into a plate 12 in the carrier 10. From the dispensing aperture 17 there enter at an inward slant two dispensing heads 56 and 57. The first can be used for dispensing a liquid into a well in the measuring position and the second for dispensing a liquid into a well adjacent to the measuring position, in particular the one which will arrive next at the measuring position. In addition, the apparatus preferably has a third dispensing head, which can be used for dispensing a liquid into a well transversely adjacent to the measuring position (in FIG. 6 behind the well being measured).

What is claimed is:

1. A fluorometer for measuring optical properties of a sample, which fluorometer has means for directing excitation light from a light source to the sample and means for directing emitted light from the sample to a detector, and a partly transparent mirror characterized in that the excitation light is directed to the sample through the mirror and the emitted light is directed from the sample via the mirror by reflection, or the excitation light is directed to the sample via the mirror by reflection and the emitted light is directed from the sample through the mirror, and that the mirror has a plurality of areas transparent to either of excitation light and emitted light or a plurality of areas non-transparent to either of emitted light and excitation light.

2. A fluorometer according to claim 1, wherein the excitation light is directed to the sample through a partly transparent mirror.

3. A fluorometer according to claim 1, wherein the transparent areas of the partly transparent mirror are substantially completely transparent to light.

4. A fluorometer according to claim 1, wherein the non-transparent areas of the partly transparent mirror are substantially completely non-transparent to light.

5. A fluorometer according to claim 1, wherein the reflective areas of the mirror are shaped so as to eliminate the effect of reflection or refraction.

6. A fluorometer according to claim 1 wherein the sample is in a vessel having a bottom, side walls and an open mouth.

7. A fluorometer according to claim 1, having means for eliminating errors caused in the emitted light by variation in the distance to the sample.

8. A fluorometer according to claim 1, having means for collimating the excitation light or means for collimating the emitted light.

9. A fluorometer according to claim 1, having a replaceable delimiter for the excitation light or a replaceable delimiter for the emitted light.

10. A fluorometer according to claim 1, having means for forming an image of the excitation light at the delimiter.

11. A fluorometer according to claim 1, having means for delimiting the emitted light and means for filtering the emitted light.

12. A fluorometer according to claim 1, having a measuring carrier in which the sample is placed, and an optics module which has a detector and optical means for directing light emitted from the sample to the detector, and which module can be placed alternatively either so that light is directed to the detector from above the sample or so that light is directed to the detector from below the sample.

13. A fluorometer according to claim 1, having a replaceable light source.

14. A fluorometer according to claim 1, wherein the mirror has reflective spots.

15. A fluorometer according to claim 14, wherein the reflective spots are approximately 1 mm in diameter.

16. A fluorometer according to claim 1, wherein the mirror has a reflective center and separate radial sectors around the reflective center.

17. A fluorometer according to claim 1, wherein the mirror has a cartwheel-shape reflective area and separate radial transparent sectors.

18. A fluorometer according to claim 1, wherein the mirror has an oval shape, the 45° projection of which is a circle.

19. A fluorometer for measuring the optical properties of a sample, having means for directing excitation light from a light source to the sample and means for directing emitted light from the sample to a detector, characterized in that the fluorometer has means for eliminating errors caused in the emitted light by variations in the distance to the sample, said fluorometer having a lens arrangement by means of which a delimited spot of excitation light is formed on the object being assayed, and said means for eliminating errors comprises a lens system for collimating emitted light and a delimiter by means of which scattered rays are delimited out of the emitted beam of light.

20. A fluorometer for measuring the optical properties of a sample, having means for directing excitation light from a light source to the sample and means for directing emitted light from the sample to a detector, characterized in that the fluorometer has means for forming an image from the light source to a delimiter, and, thereafter, the fluorometer has means for collimating the excitation light.

21. A fluorometer for measuring the optical properties of a sample, having means for directing excitation light from a light source to the sample and means for directing emitted light from the sample to a detector, characterized in that the fluorometer has means for collimating the emitted light, and in that the fluorometer further comprises a delimiter, by means of which scattered rays are delimited out from the collimated light.

22. A fluorometer for measuring the optical properties of a sample, having means for directing excitation light from a light source to the sample and means for directing emitted light from the sample to a detector, characterized in that the fluorometer has means for forming an image of the source of excitation light at a delimiter, the source of the excitation light being an incandescent bulb.

23. A fluorometer for measuring the optical properties of a sample, having means for directing excitation light from a light source to the sample and means for directing emitted light from the sample to a detector, characterized in that the fluorometer has means for delimiting the emitted light comprising an aperture and means for filtering the emitted light located at a point of the aperture, and the fluorometer comprises an arrangement for forming in the aperture an image of a delimited region of the sample.

24. A fluorometer for measuring the optical properties of a sample, having means for directing excitation light from a light source to a sample and means for directing emitted light from the sample to a detector, characterized in that the fluorometer has a replaceable source of light and in that the fluorometer has a measuring carrier and an optics module.

25. A fluorometer for measuring the optical properties of a sample, having means for directing excitation light from a light source to the sample and means for directing emitted light from the sample to a detector, characterized in that the fluorometer has a replaceable excitation light delimiter or a replaceable emitted light delimiter and in that the fluorometer has a measuring carrier and an optics module.

* * * * *

UNITED STATES PATENT AND TRADEMARK OFFICE
CERTIFICATE OF CORRECTION

PATENT NO. : 6,144,455
DATED : November 7, 2000
INVENTOR(S) : Timo Karmeniemi and Jukka Tuunanen It is certified that error appears in the above-identified patent and that said Letters Patent is hereby corrected as shown below:

Title page,
Item [56], References Cited,
Reference 4,945,250 "07/1990" should be -- 1/1990 --.

Column 2,
"25 Claims, 6 Drawing Sheets" should be -- 26 Claims, 6 Drawing Sheets" --.

Column 7, claim 5,
Line 35, "refraction" should be -- diffraction --.

Column 8,
The following claim should be added:

-- 26. A fluorometer according to Claim 19, wherein the emitted light is measured from a constant solid angle. --.

Signed and Sealed this

Twelfth Day of March, 2002

Attest:

Attesting Officer

JAMES E. ROGAN
Director of the United States Patent and Trademark Office